United States Patent
Popescu (10) Patent No.: US 9,480,414 B2
(45) Date of Patent: Nov. 1, 2016

(54) ELASTOGRAPHY METHOD, AND MAGNETIC RESONANCE SYSTEM FOR IMPLEMENTING AN ELASTOGRAPHY METHOD

(71) Applicant: Stefan Popescu, Erlangen (DE)

(72) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 589 days.

(21) Appl. No.: 13/927,401

(22) Filed: Jun. 26, 2013

(65) Prior Publication Data

US 2014/0012126 A1 Jan. 9, 2014

(30) Foreign Application Priority Data

Jul. 4, 2012 (DE) .................. 10 2012 211 581

(51) Int. Cl.

| *A61B 5/055* | (2006.01) |
| *G01R 33/563* | (2006.01) |
| *A61B 8/08* | (2006.01) |
| *A61B 5/02* | (2006.01) |

(52) U.S. Cl.
CPC ............... *A61B 5/055* (2013.01); *A61B 8/485* (2013.01); *G01R 33/56358* (2013.01); *A61B 5/02007* (2013.01)

(58) Field of Classification Search
CPC .. A61B 5/02007; A61B 5/055; A61B 8/485; G01R 33/56358
See application file for complete search history.

(56) References Cited

U.S. PATENT DOCUMENTS

| 6,974,915 B2 | 12/2005 | Brodsky et al. |
| 2003/0193336 A1 | 10/2003 | Ehman et al. |
| 2004/0199070 A1 | 10/2004 | Krockel |
| 2006/0152219 A1* | 7/2006 | Bieri ................ G01R 33/56358 324/309 |
| 2006/0264736 A1 | 11/2006 | Ehman et al. |
| 2010/0026298 A1 | 2/2010 | Wald |
| 2010/0145420 A1 | 6/2010 | Zhu et al. |
| 2011/0245658 A1 | 10/2011 | Numano et al. |
| 2011/0316539 A1 | 12/2011 | Lagendijk et al. |

FOREIGN PATENT DOCUMENTS

JP 2010227417 A 10/2010

OTHER PUBLICATIONS

"Auto-elastography of the brain", Zhao et al., Proc. Intl. Soc. Mag. Reson. Med., vol. 17 (2009) p. 713.

\* cited by examiner

*Primary Examiner* — Ruth S Smith
(74) *Attorney, Agent, or Firm* — Schiff Hardin LLP

(57) ABSTRACT

In a methods for elastography in a defined region of an examined person, a radio-frequency pulse is radiated to manipulate a transverse magnetization in the defined region and at least one additional radio-frequency pulse with a spatial selectivity of the amplitude is radiated to generate shear waves in the defined region. A magnetic resonance signal from the defined region is detected and a determination of a value describing the tissue elasticity in the defined region is made based on the magnetic resonance signal.

18 Claims, 6 Drawing Sheets

ELASTOGRAPHY METHOD, AND MAGNETIC RESONANCE SYSTEM FOR IMPLEMENTING AN ELASTOGRAPHY METHOD

BACKGROUND OF THE INVENTION

1. Field of the Invention

The present invention concerns techniques for elastography and a magnetic resonance system for implementing those techniques. More particularly, the invention concerns techniques of elastography in which shear waves are generated by a radio-frequency coil array of such a magnetic resonance system.

2. Description of the Prior Art

Elastography is a medical examination modality that allows a determination of tissue elasticity to be made. For example, magnetic resonance elastography (MRE) is a known technique that allows properties of shear waves (transverse sound waves in a frequency range of approximately 10-200 Hz) within body tissue to be detected and imaged by means of magnetic resonance signals. The shear waves are applied or generated on the outer surface of the body, for example by a mechanical vibration device. Their propagation is monitored within the body tissue by means of magnetic resonance signals that are caused to be emitted from the tissue while the waves are propagating therein. Properties of the shear waves can be indicative of a tissue rigidity or tissue elasticity. Therefore, clinical applications and diagnostics can be implemented based on the measurement of these properties.

Such MRE techniques are known from multiple sources, for example from the US Patent Application Publication No. 2003/0193336 A1. Harmonic shear waves are externally applied in order to bring the tissue into oscillation. The displacement of the tissue that results can then be detected by means of suitable magnetic resonance (MR) measurement sequences. The tissue elasticity can be quantified from the detected MR signals with a spatial resolution. Typical frequencies of the shear waves that are used are 20 Hz-200 Hz, for example. In MRE, movement-coding gradient fields ("motion-sensitizing gradients") can be used to image the tissue displacement due to the shear waves, for example.

A technically related method known as "acoustic radiation force imaging" (ARFI) images representing tissue displacement that are generated by focused ultrasound pulses with high intensity ("high intensity focused ultrasound, HIFU"). With such ARFI techniques it is possible to use focused ultrasound, i.e. longitudinal shear waves in a frequency range of greater than 1 MHz (pressure wave), to generate shear waves with relatively low frequencies. Motion-sensitizing gradient fields can also be used for imaging the tissue displacement.

An additional technique to image focused ultrasound pulses is known from US 2010/0026298 A1 and U.S. Pat. No. 7,956,613 B2.

Spin-lock measurement sequences are used in connection with focused ultrasound pulses to image the tissue displacement, such as for the purpose of destroying tumors by means of thermal ablation.

Such known techniques have a number of disadvantages. For example, the shear waves or ultrasound waves are typically generated and applied at the surface of the body by means of mechanical vibration devices or by means of ultrasound emitters. In general, these devices for generation are not compatible (or are compatible only to a limited extent) with the environment within an MR system. Susceptibility artifacts can arise in the MR signals that are generated in the presence of such devices, or specially designed and thus expensive equipment must be used that is more MR-compatible. Special solutions are then required that complicate the clinical workflow and produce further limitations with regard to the space available to the patient within the magnetic resonance tube. Moreover, the additional components that are necessary produce increased costs in implementation, as well as increased costs for procurement and servicing.

Space problems also can arise due to the use of mechanical vibration devices or ultrasound emitters. Within the scope of a magnetic resonance measurement (data acquisition) sequence, it can be desirable to place a local coil or a local coil array near the surface of the body of the patient. Since the mechanical vibration devices or ultrasound emitters are most advantageously placed at such locations, the space problems can result.

Moreover, shear waves and/or ultrasound waves exhibit a relatively high attenuation during propagation through the tissue. For example, from experiments it is known that shear waves above an eigenfrequency of 200 Hz (which corresponds to a wavelength of 1 to 3 cm) are absorbed rapidly within the tissue and therefore cannot be used in deep tissue layers (i.e. far removed from the site of generation at the skin surface of the patient). This is because shear waves or ultrasound waves are generated by mechanical vibration devices or ultrasound emitters located on the surface of the patient, and must first travel a certain distance within the tissue before they arrive at the relevant sample site or measurement region.

The use of low-frequency shear waves (for example below 35 Hz, which corresponds to a wavelength of 6 to 17 cm), however, significantly reduces the achievable spatial resolution. For example, this can hinder or make impossible the detection of smaller tumors, or generally limit the diagnosis evaluation capability. Moreover, given the use of such low-frequency shear waves, the contrast in MRE images is not solely dependent on the acoustic properties of the tissue, but also is a function of the resulting wavelength within the body. For example, standing waves can arise in resonators that are formed by the tissue structure. This can complicate the clinical interpretation of the MRE images or make it impossible.

SUMMARY OF THE INVENTION

Therefore, a need exists for improved elastography techniques. In particular, a need exists for improved elastography techniques using a magnetic resonance system that allow a high precision in the determination of a variable describing tissue elasticity and for techniques that enable simpler and more cost-effective elastography.

According to a first aspect, the invention concerns a method for elastography in a defined region of an examined person using a magnetic resonance (MR) system. The method includes the radiation of a radio-frequency (RF) pulse to manipulate a transverse magnetization in the defined region; and the radiation of at least one additional RF pulse with a spatial selectivity as to amplitude in order to generate shear waves in the defined region. The method furthermore includes the detection of an MR signal of the transverse magnetization from the defined region, which makes the shear waves visible, and the determination of a value describing the tissue elasticity in the defined region, based on the MR signal.

The shear waves can be transverse sound waves with a frequency of approximately 1-300 Hz. In other words, the spatial selectivity of the amplitude of the at least one additional RF pulse can correspond to at least one additional focused RF pulse. The spatial selectivity of the amplitude is preferably a spatial selectivity of the amplitude of the electric field component of the RF electromagnetic field. The radiation of the at least one additional RF pulse with a spatial selectivity of the amplitude can influence a spatial distribution of the shear waves, for example.

In other words, the MR signal that makes the shear waves visible can be indicative of at least one parameter of the shear waves. For example, the MR signal can be indicative of an amplitude of the shear waves.

The examined person can be located, for example, on a positionable table in the MR system. The transverse magnetization (magnetization of the nuclear spins—typically of 1-H—orthogonal to the basic magnetic field of the MR system) can then be generated and/or detected in a defined region using conventional motion-sensitizing gradient fields (phase selection, frequency selection, slice selection). For example, the RF pulse to manipulate the transverse magnetization can be an excitation pulse to generate the transverse magnetization; or a refocusing pulse; or a 90° pulse; or an alpha pulse with a deflection smaller than 90°; or another pulse that has an interaction with the nuclear magnetization. For example, the RF pulse to manipulate the transverse magnetization can have a frequency that is identical to the nuclear magnetic resonance frequency. Suitable RF pulses are known to those skilled in MR techniques and MR measurement sequences. In general, more than a single RF pulse can be used to manipulate the transverse magnetization, for example 2 or 3 RF pulses. This can be dependent on the MR measurement sequence that is used to excite and detect the transverse magnetization.

For example, a temporary localized heating of the tissue can be produced by the energy transferred or focused by the at least one additional RF pulse. The tissue can thereby expand. The mechanical expansion can generate the shear wave. The shear waves can describe a deflection of the material as a function of space and time. The group velocity of the shear wave in biological tissue can typically amount to approximately 2 m/s. The group velocity can be a function of the wavelength, and the wavelength can in turn be determined by the at least one additional RF pulse, namely its spatial selectivity. The generation of the shear wave directly in the determined region results in the shear wave being exposed to less damping during propagation in the defined region in comparison to techniques that generate the shear wave at the skin surface.

For example, it is possible for the radio-frequency pulse and/or the at least one additional radio-frequency pulse to be radiated using a radio-frequency coil array of the magnetic resonance system. For example, the RF coil array can be permanently installed in the MR system or can be a local RF coil array that can be arranged near the surface of the body of the examined person.

Alternatively, for example, it would be possible to use a body coil of the MR system, which is larger (and therefore has a small spatial dependency of the amplitude) for the RF pulse to manipulate the transverse magnetization, while using the RF coil array for the radiation of the at least one additional RF pulse to generate the shear waves.

For example, both the radio-frequency pulse and the at least one additional radio-frequency pulse can be radiated using one and the same radio-frequency coil array of the MR system. For example, such radio-frequency coil arrays are known for image-accelerated parallel MR measurement sequences (known as PPA acquisition methods such as GRAPPA, SENSE or SMASH etc.), with an undersampling of k-space. Such RF coil arrays can have respective sensitivity maxima of the individual coils at different locations, and a relatively strong dependency of the sensitivity on location (particularly in comparison to the body coil). The use of a single RF coil array simplifies implementation of the elastography since (for example) no separate parts (for example mechanical vibration device) are necessary. This can also reduce the cost of a corresponding MR system.

The spatial selectivity of the amplitude of the at least one additional RF pulse can be achieved by a defined amplitude relationship and/or phase relationship between the various coils of the RF coil array, for example. Constructive and destructive interference can have the effect that a significant amplitude (for example of the electric field) is essentially limited to the defined region. In other words, the spatial selectivity of the excitation can produce a markedly pronounced local maximum of the amplitude of (for example) the electric field of the at least one additional RF pulse, i.e. a heating of tissue that is clearly defined and delimited in positional space, thus a focusing of the at least one additional RF pulse. For example, a sufficiently high amplitude of the generated shear waves can be achieved even with moderate RF power, which presents a low health risk to the patient, since only a minor (in comparison to the body temperature) local heating of the tissue occurs. A wide variety of techniques to generate the spatial selectivity of the amplitude of the additional RF pulse are known to those skilled in the art, for example from WO 03/002199 A2.

Moreover, the spatial selectivity of the generation of the shear waves allows the shear waves to be generated directly in the defined region, i.e. at the location at which the elastography is implemented. In comparison to conventional techniques that are based on a generation of the shear waves at the skin surface of the examined person by means of mechanical vibration devices, for example, a sufficiently high amplitude of the shear waves in the defined region can be ensured without the attenuation of the shear waves on their way from the skin surface to the defined region needing to be taken into account. In particular, shear waves can be used in a broader and/or higher frequency range, and in fact even at frequencies at which an attenuation of the shear waves in tissue is high.

A wide variety of techniques that allow the detection of the MR signal in order to make the shear waves visible are known to those skilled in the art. For example, this can be accomplished by means of the aforementioned, motion-sensitizing gradient fields and/or by means of the spin-lock sequences. In this regard, in various embodiments the radiation of the at least one additional radio-frequency pulse can occur simultaneously, at least in part, with the radiation of the RF pulse to generate the transverse magnetization.

It can be useful for the carrier frequency of the at least one additional RF pulse to be different from the resonance frequency of the transverse magnetization (magnetic resonance frequency). For example, the resonance frequency of the transverse magnetization can be identical to the carrier frequency of the RF pulse used to manipulate the transverse magnetization. For example, a different carrier frequency can mean that the carrier frequency of the additional RF pulse is outside of or well outside of a line width of the resonance frequency of the relevant nuclear spins. For example, the resonance frequency of the nuclear spins can typically be at 64 MHz for a 1.5 Tesla MR system. It can therefore be possible to select the carrier frequency of the at least one additional excitation pulse to be different from this value.

For example, the shear waves can be quasiplanar shear waves, and the radiation can include the sequential radiation of multiple additional radio-frequency pulses with a maximum of the amplitude at respective different locations, with the different locations being spaced essentially parallel to a wave front of the quasiplanar shear wave. For example, the locations can be situated within the defined region. For example, quasiplanar shear waves have the advantage that they have a relatively larger amplitude, i.e. a greater oscillation of the material. This can produce a larger spatial decay length, i.e. a smaller attenuation. This can also increase the signal in the elastography.

A wave front of the quasiplanar shear wave can be generated by the sequential radiation of the multiple additional separated RF pulses. For example, it is possible for a quasiplanar wave front to be generated by a slight time offset between the sequentially radiated, separated multiple additional RF pulses. However, since a (relatively small) time offset can remain due to technical limitations, a slight angle can exist between the propagation direction and the direction of the sequentially radiated additional RF pulses. The angle can be a few degrees.

In general, it is possible to precisely radiate the additional RF pulse with a defined pulse width to generate pressure waves in the defined region. If the tissue is irradiated with a single additional RF pulse, the tissue heats locally and expands. This thermal expansion generates pressure waves, and the frequencies of the pressure wave can extend in a range from 0 . . . 1/(pulse width). In other words, shorter additional RF pulses can generate a wider range of frequencies of the pressure waves. This results from the principle of Fourier transformation between time duration of the excitation and width of the excitation in frequency space (frequency domain). For example, an additional RF pulse with a pulse duration of 1 μs can generate pressure waves with frequencies up to 1 MHz. Corresponding principles apply to the excited wavelengths that can result from a Fourier-transformed profile of the spatial selectivity of the amplitude.

Shear waves can arise from the radio-frequency pressure waves by various physical processes (which need not be explained in detail herein). A pulse-shaped shear wave or a pulse-shaped shear wave front can be generated by the radiation of a single additional RF pulse, or multiple sequential additional RF pulses in rapid succession. This can also have a significant frequency bandwidth.

In various embodiments it can be desirable to not produce pulse-shaped shear waves that have a significant frequency bandwidth as described above, in various embodiments that relate to a shear wave with a defined repetition rate (i.e. a defined frequency) or a low frequency bandwidth.

It is also possible for the sequential radiation for the multiple additional RF pulses to repeat with an additional frequency. For example, the additional frequency can be determined depending on a wavelength of the quasiplanar shear wave and/or a spatial resolution of the elastography. The additional frequency preferably is in the range of 20-400 Hz, and more preferably in the range from 50-150 Hz.

The additional frequency can thus define a repetition rate of the sequential radiation of the multiple additional RF pulses. By the repeated sequential radiation of the multiple additional RF pulses with the repetition rate or the additional frequency, quasiplanar shear waves are generated with a relatively low frequency width. In other words: a quasiplanar shear wave with a defined frequency can be generated by the repeated sequential radiation. This makes it possible to implement the elastography with frequency resolution. This can be advantageous with regard to a spatial resolution of the MR signal, and therefore with regard to the elastography data. The signal-to-noise ratio of the elastography can also be increased by spatially resolved measurement. For example, advantageous results with regard to the spatial resolution of the elastography and/or an attenuation of the shear waves can be generated by the selection of the additional frequency, i.e. the frequency of the quasiplanar shear wave, in the aforementioned range. This makes it possible to optimize the signal-to-noise ratio of the elastography.

The preceding discussion primarily concerned properties of the shear waves and the techniques to generate the shear waves. The MR measurement sequence and the detection of the MR signal are discussed in the following.

For example, the radiation of the radio-frequency pulse and the detection of the magnetic resonance signal can occur within the scope of an MR measurement sequence, which can be a spin echo sequence or a spin-lock sequence. Such MR measurement sequences are known to those skilled in the art and need not be explained further herein.

For example, the repetition rate of the MR measurement sequence for different slices within the defined region and/or different defined regions and the additional frequency can be matched to one another.

It can be desirable to repeat the MR measurement sequence with the repetition rate to detect MR signals, for example for different defined regions and/or different slices within the defined region (different slice-selection gradient fields). It can then be desirable for the frequency of the shear wave to be synchronized with the repetition rate in order to enable a continuous excitation of the shear wave. A continuous resonant generation of the shear wave can therefore be achieved, and a fixed phase relationship with the MR measurement sequence (i.e. generation, influencing and detection of the transversal magnetization) can be maintained. For example, the repetition rate of the MR measurement sequence can be a whole-number multiple of the additional frequency, i.e. of the repetition rate of the sequential radiation of the multiple additional RF pulses. In other words: the MR measurement sequence can have a fixed phase relationship with the excited shear wave. For example, the detection of the MR signal and/or the radiation of the RF pulse to manipulate the transversal magnetization can respectively take place at the same or corresponding phases of the shear wave.

Alternatively, the generation of the shear wave can be triggered the radiation of the at least one additional RF pulse respectively at the beginning of an MR measurement sequence (for example for a slice of the defined region or various defined regions). It can then be unnecessary to maintain a coherent shear wave over the entire duration of the elastography measurement.

For example, the MR measurement sequence can be the spin-lock sequence with a spin-lock preparation pulse, and the radiation of the at least one additional RF pulse can occur during the spin-lock preparation pulse. During the spin-lock phase, the RF pulse to generate the transversal magnetization can include the radiation of a continuous RF wave, for example with the nuclear spin resonance frequency. For example, an amplitude of the spin-lock preparation pulse can be matched to the additional frequency with which the multiple additional RF pulses are repeatedly radiated.

For example, such techniques are fundamentally known with regard to what is known as "rotary saturation imaging" (RSI). Such techniques can provide comparably high sensitivity in the detection of the tissue movement. This means that a signal-to-noise ratio of the elastography can be comparably high. Moreover, such techniques can avoid the use of motion-sensitizing gradient fields with a large time dependency (fast switching of the gradient fields), which can prevent acoustic noise or vibrations that are transferred to the patient body during the elastography. This can prevent an interference of the vibrations with the elastography measurement. Patient comfort can also be increased.

The MR measurement sequence alternatively can be a spin echo sequence with motion-sensitizing gradient fields, with the radiation of the at least one additional RF pulse occurring during the motion-sensitizing gradient fields. For example, the repeated sequential radiation of the multiple additional RF pulses can occur in the third quarter of each of the periods or the duration of the motion-sensitizing gradient fields.

For example, the motion-sensitizing gradient fields can be added to a conventional spin echo sequence in the slice-selection direction in order to code tissue displacement along the energy movement direction (orthogonal to the wave fronts) of the quasiplanar shear wave. The at least one additional RF pulse to generate the shear wave can be activated during the third quarter of every period of the (for example sinusoidal, motion-sensitizing) gradient fields in order to generate synchronous tissue movement and keep the pulse duty factor of the at least one additional RF pulse as low as possible. In this embodiment it is also possible to select the carrier frequency of the at least one additional RF pulse to be sufficiently unequal to the nuclear spin resonance frequency in order to avoid interferences.

For example, a duration and/or amplitude of the at least one additional radio-frequency pulse can be defined depending on an estimated amplitude of the generated shear wave. In other words: it can be possible to limit the RF energy that is used to a necessary extent which provides an amplitude of the shear wave that allows a sufficiently high signal-to-noise ratio of the elastography. Higher amplitudes can be avoided in order to limit the temperature increase in the tissue of the examined person.

For example, a duration and/or an amplitude of the at least one additional radio-frequency pulse can be determined based on an estimated heating of tissue in the defined region, wherein the heating is less than 1 K (preferably less than 10 mK, more preferably approximately 1 mK). For example, this can correspond to an acoustic pressure in a range of approximately 1-10 mbar or approximately 8 mbar (800 Pa). Moreover, this can be contrasted with hyperthermal treatment of tumors, for example, where a heating of the tissue by multiple Kelvin (up to multiple tens of Kelvin) is used. A damage to the examined tissue can therefore be avoided while a sufficiently high signal-to-noise ratio can nevertheless be achieved in the elastography.

According to a further aspect, the invention concerns the use of a radio-frequency coil array of a magnetic resonance system to generate shear waves in a defined region of an examined person by radiation of at least one additional radio-frequency pulse with a spatial selectivity of the amplitude.

For example, this use can include a method for elastography according to a further aspect of the invention. For such a use of the RF coil array, effects can be achieved which are comparable to the effects that can be achieved with the method for elastography according to the further aspect of the invention.

According to a further aspect, the invention concerns a use of a radio-frequency coil array of a magnetic resonance system for elastography by means of generation of shear waves in a defined region of an examined person by radiation of at least one additional radio-frequency pulse with a spatial selectivity of the amplitude.

For example, given such an additional RF pulse a produced heating in the tissue can be approximately 1 mK, or in the range from 1 mK to 1 K or more. A heating to approximately 40-120° C. can occur, for example.

According to a further aspect, the invention concerns an MR system that is configured to implement elastography in a defined region of an examined person. The MR system has a radio-frequency coil array that is operated to radiate a radio-frequency pulse to manipulate a transversal magnetization in the defined region, and radiate at least one additional radio-frequency pulse with a spatial selectivity of the amplitude to generate shear waves in the defined region. The MR system furthermore has a reception unit that detects a magnetic resonance signal of the transverse magnetization from the defined region, which makes the shear waves visible. The MR system furthermore has a computer configured to determine a value describing the tissue elasticity in the defined region, based on the magnetic resonance signal.

The invention also encompasses a method for elastography in a defined region of an examined person, that includes: radiating an RF pulse to manipulate a transverse magnetization in the defined region, and radiating at least one non-ionizing laser pulse at the examined person to generate shear waves in the defined region. The method furthermore includes detection of an MR signal of the transverse magnetization from the defined region that makes the shear waves visible, and the determination of a value describing the tissue elasticity in the defined region, based on the MR signal.

Suitable techniques to generate the shear waves by the laser pulse are known to those skilled in the art, such as in connection with photoacoustic imaging, and therefore need not be explained further in this context. It should be understood that the features that can be combined with regard to shear waves that were generated by means of the at least one additional RF pulse can be combined with the features for the presently discussed aspect, in which the shear waves are generated with the at least one laser pulse.

According to a further aspect, the invention concerns a magnetic resonance system to implement elastography in a defined region of an examined person that includes a computer to control an RF signal generator that is coupled with an RF coil array. The computer is configured to cause the magnetic resonance system to radiate a radio-frequency pulse to manipulate a transverse magnetization in the defined region; and radiate at least one additional radio-frequency pulse with a spatial sensitivity of the amplitude to generate shear waves in the defined region. The magnetic resonance system furthermore has a reception unit that detects a magnetic resonance signal of the transverse magnetization from the defined region, which makes the shear waves visible. The computer is furthermore configured to determine a value describing the tissue elasticity in the defined region, based on the magnetic resonance system.

Naturally, the features of the previously described embodiments and aspects of the invention can be combined with one another. In particular, the features can be used not only in the described combinations but also in other combinations or independently, without departing from the scope of the invention.

DESCRIPTION OF THE PREFERRED EMBODIMENTS

The present invention is explained in detail in the following using preferred embodiments with reference to the drawings. In the figures, identical reference characters designate identical or similar elements.

Figure 1:
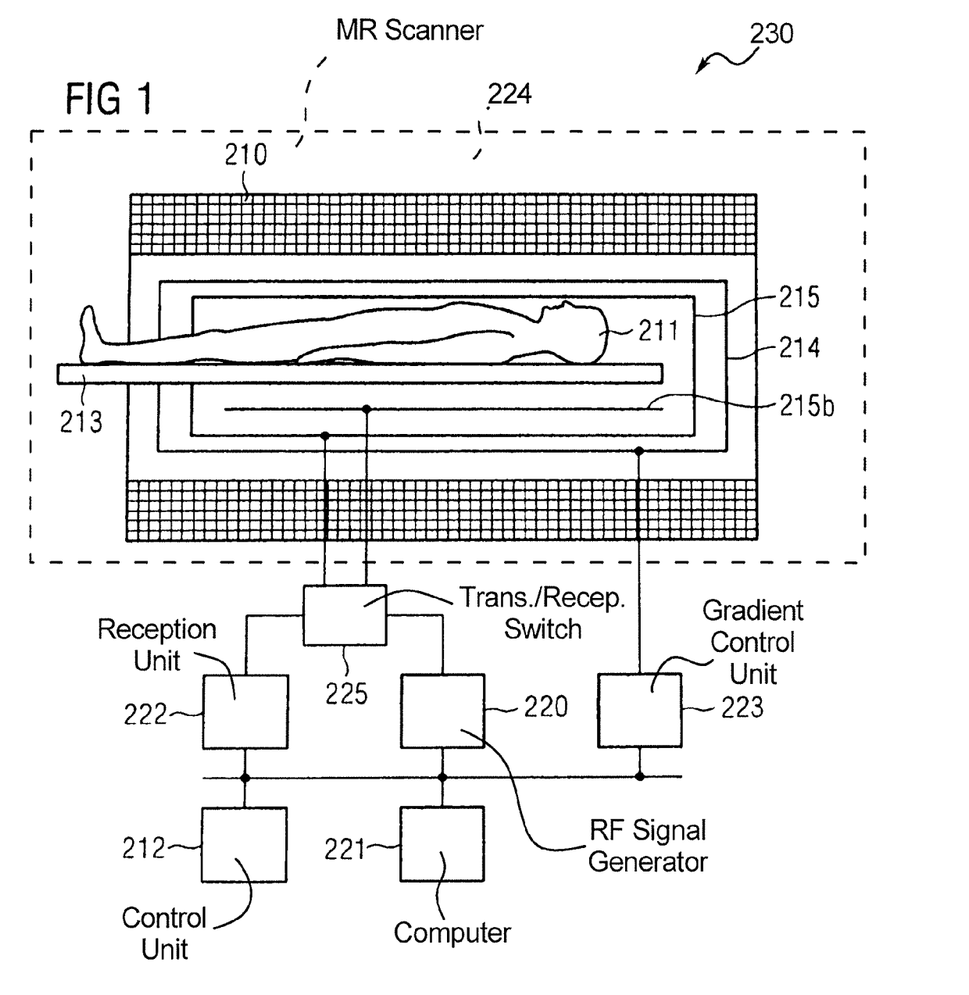
FIG. 1 schematically illustrates an MR system which is suitable to implement techniques for elastography according to the invention.

FIG. 1 schematically shows a magnetic resonance (MR) system 230 according to an embodiment of the present invention. The MR system 230 has a magnet 210 to generate a basic magnetic field. For example, the magnet 210 can be a tube magnet and the basic magnetic field can be situated parallel to the longitudinal axis of the tube. An examination subject—here an examined person 211—can be slid on a bed table 213 into the magnet 210. The MR system 230 furthermore has a gradient system 214 to generate magnetic field gradients that are used for imaging and for spatial coding of detected MR signals. The gradient system 214 typically comprises at least three separately controllable coils or coil sets that are operated by a gradient control unit 223 enable gradient fields to be applied and switched along defined spatial directions (gradient axes). Those components within the dashed outline 224 are commonly called an MR scanner.

The MR system 230 also has an RF signal generator 220 and a reception unit 222 that are coupled via a transmission/reception switch 225 with both an RF coil array 215 and a body coil 215b of the MR system 230. It is possible to radiate RF pulses via the coils 215, 215b by means of the RF signal generator 220. The RF pulses can be amplitude-modulated and have a defined carrier frequency. The reception unit 222 detects RF signals (for example the relaxing transversal magnetization) as inductive voltages at the coils 215, 215b.

The MR system 230 furthermore has a control unit 212 (which can comprise a keyboard, a mouse, connection interface etc., for example) in order to enable an interaction or control of the MR system with and by a user. Moreover, the MR system 230 has a computer which is set up to control MR measurement sequences (i.e. to control the units 220, 222, 223), for example. Moreover, the computer 221 is configured to determine a tissue elasticity in an elastography measurement of the examined person 211 with spatial resolution.

The general functioning of such an MR system 230 is known to those skilled in the art, such that additional details are not necessary herein. The units of the MR system 230 were presented and discussed separately in FIG. 1. However, specific units can be combined and/or functionally integrated, for example as hardware and/or software. For example, this can be the case for the computer 221, which can be a part of a system computer of the MR system 230.

Figure 2:
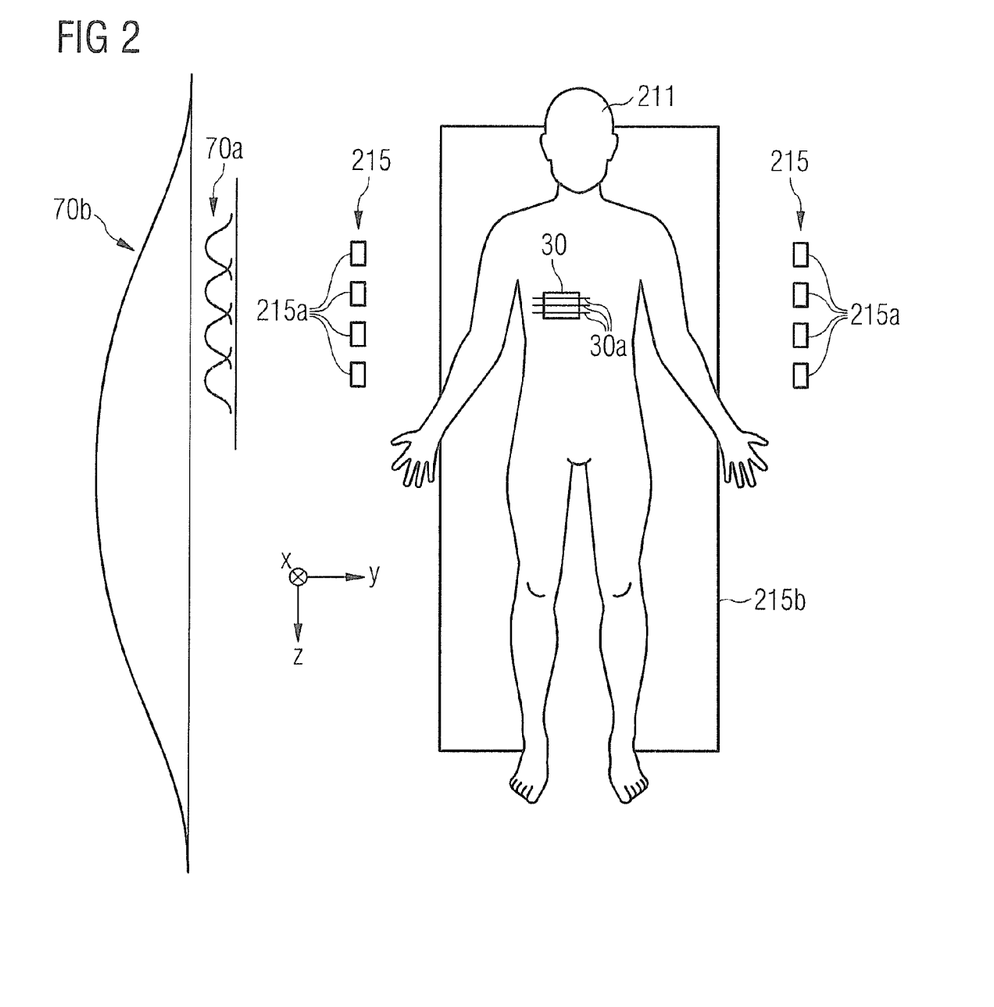
FIG. 2 illustrates a radio-frequency coil array of the MR system of FIG. 1.

Individual coils 215a of the RF coil array 215 and the examined person 211 are shown in FIG. 2. The coils 215a of the RF coil array 215 can be arranged as an array in the surroundings of the examined person 211. In particular, the coils 215a can have a maximum sensitivity 70a at different locations. In comparison to the sensitivity 70b of the body coil 215b, the sensitivities of the coils 215a can have a stronger spatial dependency.

For example, via suitable activation of the individual coils 215a (i.e. via a defined amplitude relationship and phase relationship) it can be possible to generate a maximum of the RF amplitude (in particular the electrical field component) at defined locations in a defined region 30 inside the examined person 211 via constructive and destructive interference. In other words: at least one additional RF pulse can be radiated by means of the RF coil array 215 with a spatial sensitivity of the amplitude in the defined region 30. Corresponding techniques to focus the RF energy by means of phase-coherent activation of the coils 215a are known to those skilled in the art, for example in relation to a hyperthermal treatment. These techniques therefore do not need to be discussed further here.

The RF coil array 215 of the MR system 230 can in particular be used to radiate at least one additional RF pulse with the spatial sensitivity of the amplitude in the defined region 30 to generate shear waves. The shear waves can designate a periodic motion of the tissue of the examined person 211, which is achieved via a time- and space-dependent deflection of the tissue. The frequency of the shear waves can be in the range from 1-300 Hz, for example. The generated shear waves can be used for elastography in various embodiment. In elastography, the different acoustic impedance of organs is used for contrast generation. The elastography can quantify the tissue elasticity or, respectively, provide a value proportional to the tissue elasticity.

Figure 3:
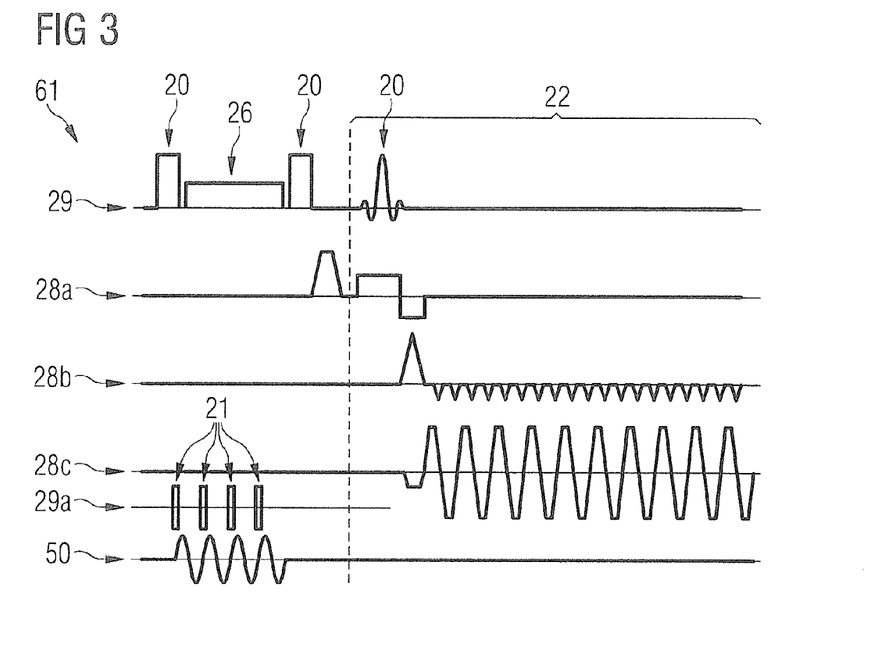
FIG. 3 illustrates a spin-lock MR measurement sequence for elastography according to the invention.
Figure 4:
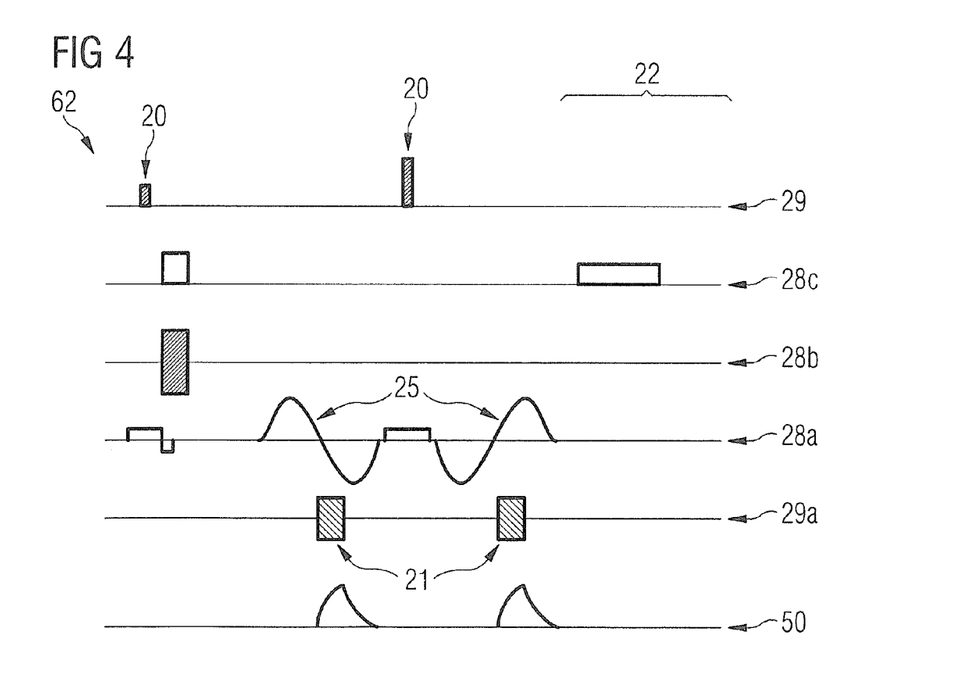
FIG. 4 illustrates a spin echo MR measurement sequence for elastography according to the invention with motion-sensitive gradient fields.

For elastography, MR measurement sequences can be used which include the radiation of an RF pulse to generate a transversal magnetization in the defined region 30, as well as the detection of an MR signal of the transversal magnetization in the defined region 30. The MR signal is indicative of the tissue movement, thus makes the shear waves visible or, respectively, images these. Techniques that allow this are discussed in relation to FIGS. 3 and 4. These MR measurement sequences can detect respective MR signals from a defined slice 30a in the defined region 30, for example by the use of different slice selection gradient fields. For example, it is possible to execute these MR measurement sequences iteratively and repeatedly for different slices 30a and/or repeatedly for different regions 30. FIGS. 3 and 4 are not to be construed as limiting in this regard.

A spin-lock MR measurement sequence 61 is shown in FIG. 3. The radio-frequency channel 29, the slice selection gradient channel 28a, the phase selection gradient channel 28b and the readout gradient channel 28c are shown. Moreover, an additional RF channel 29a is shown. A first 90° x RF pulse 20 is radiated (for example by means of the RF coil array 215 or by means of the body coil 215b) and a continuous spin-lock preparation pulse 26 subsequently acts on the transversal magnetization (magnetization component orthogonal to the basic magnetic field) that is thereby generated. The surviving transversal magnetization is then switched again in the longitudinal direction (parallel to the basic magnetic field) by means of a 90° −x RF pulse 90. The detection of the MR signal then takes place in a detection phase 22. Such techniques are also known as rotation-saturation imaging (RSI). A gradient known as a "spoiler gradient" is applied along the gradient field axis 28a between the 90° −x RF pulse 20 and the detection phase 22 in order to destroy any transverse magnetization that still remains. Any suitable MR imaging frequency (for example an EPI sequence as in the case of FIG. 3) can be implemented during the detection phase.

The radiation of four additional RF pulses 21 to generate the shear waves takes place during the spin-lock preparation pulse 26. The multiple additional RF pulses 21 can also be radiated with the coil array 215 of the MR system 230. The four respective multiple additional RF pulses 21 are radiated with an additional frequency or, respectively, a defined repetition rate; this additional frequency determines the frequency of the shear waves 50 (see below in FIG. 3). An amplitude of the spin-lock preparation pulse 26 can be matched to the additional frequency with which the additional RF pulses 21 are radiated, such that a Larmor frequency is identical to the additional frequency of the additional RF pulses 21 in the rotating reference system of the transversal magnetization.

An alternative embodiment—namely a spin echo MR measurement sequence 62—is shown in FIG. 4. A 180° RF refocusing pulse follows the 90° RF pulse. Both RF pulses 20 are applied at the spin resonance frequency. Sinusoidal, motion-sensitizing gradient fields 25 along the slice selection direction 28a are additionally added to the conventional spin echo measurement sequence 62. These motion-sensitizing slice selection gradient fields 25 code the displacement of tissue along the propagation direction of the shear waves. Two additional RF pulses 21 are activated during the third quarter of every motion-sensitizing gradient field 25 to generate synchronous tissue movement 50. It should be understood that it can be possible to apply the RF pulses 20 as well as the additional RF pulses 21 with the RF coil array 215.

Two special MR measurement sequences for elastography are shown in FIGS. 3 and 4, but, it should be understood that any known MR measurement sequence suitable for elastography can be used (for example for shear waves that are generated by mechanical vibration devices) and be combined with the techniques according to the invention for generation of shear waves. This is the case since the use of the RF coil array 215 according to the invention for radiation of the additional RF pulses 21 can generate shear waves within the scope of a wide variety elastography techniques.

It should be understood that the techniques for elastography that are discussed in the preceding can be used to generate the shear waves by means of the RF coil array 215 of the MR system 230 that is already present anyway. It is thus not necessary to provide special mechanical vibration devices that, for example, complicate the workflow during the elastography and can make additional steps necessary. In contrast to conventional elastography techniques (in particular magnetic resonance elastography), according to the invention it can be possible to use RSI MR measurement sequences (see FIG. 3) to improve the sensitivity of the motion detection. An increased sensitivity with regard to tissue vibration can be achieved in contrast to thermoacoustic imaging techniques that are based on acoustic transducers that are placed on the body surface in order to detect vibrations deep within the body. This is the case since the shear waves can be generated directly in the defined region 30 and be detected (via the transversal magnetization). Given thermoacoustic imaging methods, however, the shear wave must traverse a propagation path from the defined region 30 to the skin surface and is hereby attenuated. This can reduce the signal-to-noise ratio. In particular, with the techniques according to the invention it can be possible to generate the shear waves without mechanical vibration devices and without contact. This can increase the patient comfort. Moreover, the techniques according to the invention are compatible with therapy techniques (such as hyperthermia or tumor ablation) without a hardware refitting being necessary.

Figure 5:
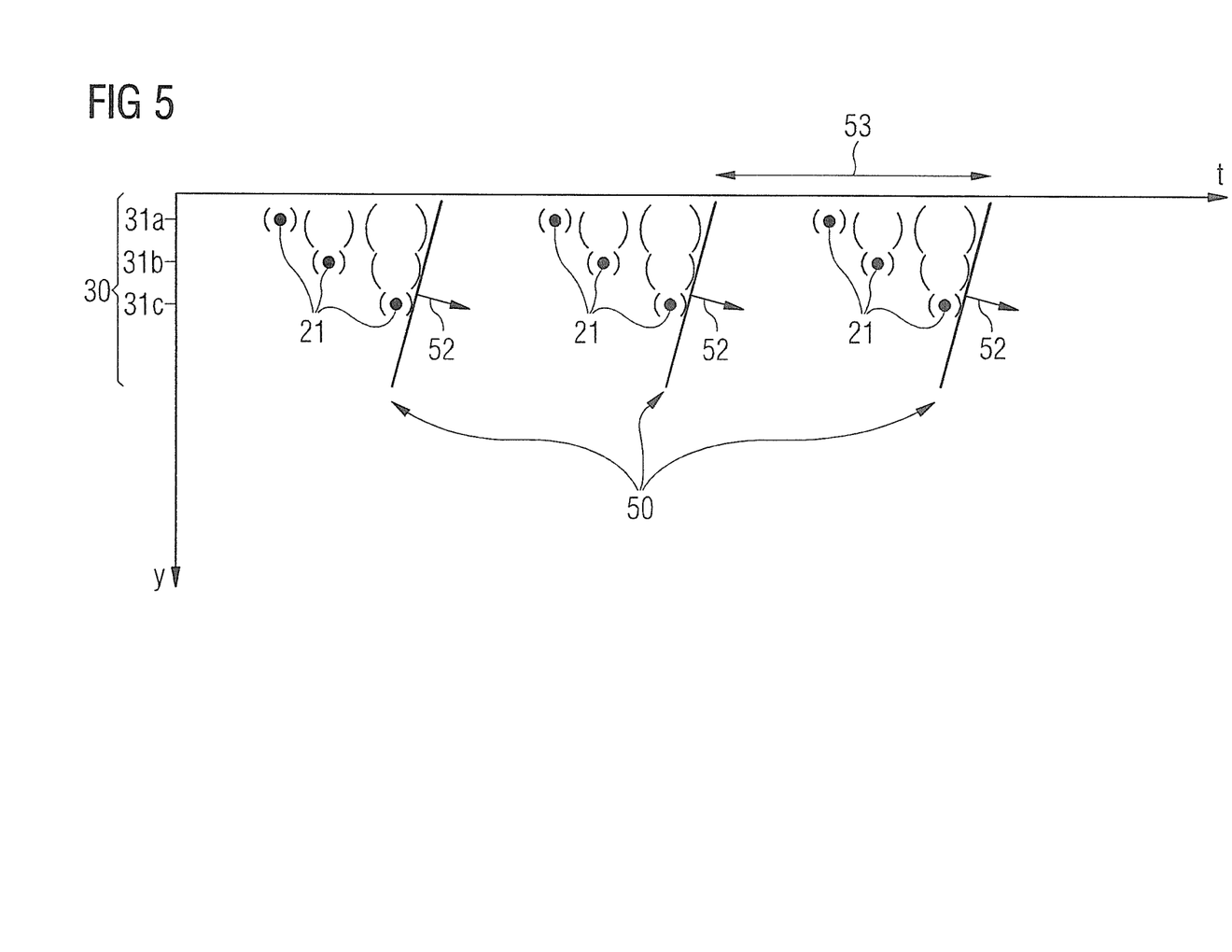
FIG. 5 illustrates the repeated sequential radiation of multiple additional RF pulses to generate a quasiplanar shear wave with a defined frequency.

The generation of the shear waves via the sequentially radiated multiple additional RF pulses 21 is subsequently discussed in detail in FIGS. 3 and 4. A time/space diagram is shown in FIG. 5. Multiple additional RF pulses 21 (represented as points in FIG. 5) are radiated sequentially at different locations 31a-31c, essentially in parallel with such a defined wave front 52 of the shear waves 50. A quasiplanar shear wave 50 thereby arises that propagates orthogonal to the direction of the wave fronts 52. The spatial sensitivity of the additional RF pulses 21 illustrated by the limited extent of the excitation points on the spatial axis (vertical axis). The spatial sensitivity is achieved via constructive and destructive interference of the signals coherently radiated by the various coils 215a of the RF coil array 215. Corresponding techniques are known to those skilled in the art. In particular, the carrier frequency of the additional RF pulses 21 can be selected so that no interference with the resonance frequency of the nuclear spins occurs, thus for example sufficiently outside of a corresponding line width of the nuclear magnetic resonance and its harmonic components.

The sequential radiation is repeated with an additional frequency 53 (the directly corresponding period duration or, respectively, repetition rate is shown in FIG. 5). The additional frequency 53 can determine a frequency of the quasiplanar shear wave 50, and a wavelength via the dispersion relationship. The additional frequency 53 can therefore correlate with an achievable spatial resolution in the elastography. Moreover, a spatial attenuation and/or a temporal relaxation of the amplitude of the quasiplanar shear wave can depend on the wavelength/the additional frequency 53. Therefore, the additional frequency 53 is established depending on the wavelength and/or the spatial resolution and/or the attenuation. For example, the additional frequency 53 can be between 50 and 150 Hz; frequencies in the range around 100 Hz are particularly advantageous.

The duration and intensity of the additional RF pulses 21 is adjusted in order to generate shear waves 50 with suitable amplitude. For example, it can be possible to determine the amplitude of the quasiplanar shear waves 50 via the local heating of the tissue upon radiation of the additional RF pulses 21. In other words: the amplitude of the shear waves can be determined via the duration and/or the amplitude of the additional RF pulses 21. For example, these parameters can be selected such that the local heating of the tissue is markedly less than 1 K, advantageously is less than 10 mK, or particularly advantageously is approximately 1 mK. In particular, such values are significantly lower than the values used for hyperthermal treatment or tumor ablation. A damage to the tissue can therefore be prevented.

For example, the radiation of the multiple additional RF pulses 21 with the additional frequency 53 can take place continuously, for example essentially over the entire time duration of the elastography measurement. In particular, MR signals for the multiple slices 30a in the defined region 30 or for multiple defined regions 30 can be acquired within the scope of the elastography measurement. However, it is also possible to trigger the radiation of the multiple additional RF pulses 21 at the beginning of an MR measurement sequence 61, 62. These techniques are subsequently discussed in FIGS. 6 and 7.

Figure 6:
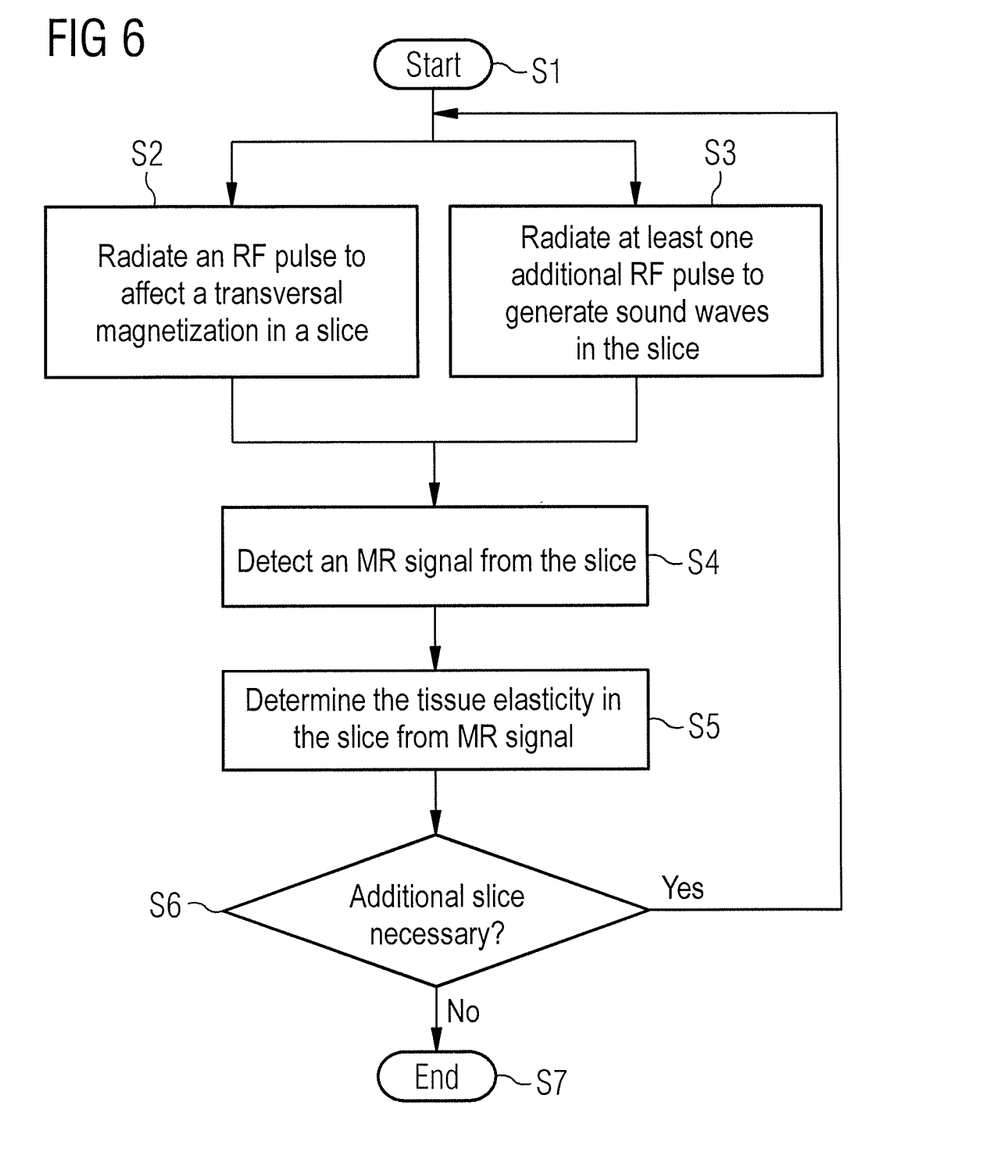
FIG. 6 is a flow chart of a method according to the invention for elastography.

FIG. 6 is a flow chart of a method according to the invention for elastography. The method begins in Step S1. The radiation of the RF pulse 20 to generate a transversal magnetization in a slice 30a in the defined region 30 of the examined person 211 takes place in Step S2. Step S2 can furthermore optionally include multiple RF pulses 20 to modify or influence the transverse magnetization, for example in particular a spin-lock preparation pulse 26. It is also possible to apply/activate motion-sensitizing gradient fields within Step S2. The radiation of the at least one additional RF pulse 21 to generate the shear waves 50 takes place in Step S3. Multiple additional RF pules 21 are advantageously repeatedly and sequentially radiated with the additional frequency 53 in order to generate quasiplanar shear waves 50. For example, the radiation of the at least one additional RF pulse 21 can occur during the spin-lock preparation phase 26 in the spin-lock MR measurement sequence 61. It is also possible that the radiation of the at least one RF pulse in Step S3 occurs in defined phases of the sinusoidal motion-sensitizing gradient fields 25, for example of a spin echo MR measurement sequence 62. In any case, in the embodiment of FIG. 6 the radiation of the RF pulse 20 to manipulate the transversal magnetization of the radiation of the at least one additional RF pulse 21 can be triggered to generate the shear waves 50 successively.

The tissue movement can therefore be synchronized with the MR measurement sequence 61, 62. The detection of the MR signal can then take place in Step S4 (for example in a detection phase 22) so that it is indicative of the shear wave 50 (i.e. makes this visible). For example, the detection phase 22 can correspond to conventional gradient echo techniques or spin echo techniques.

A value proportional to the tissue elasticity—for example in particular the tissue elasticity itself—is determined in Step S5 from the MR signal (for example by means of the computer 221). In the case of the spin-lock measurement sequence 61, for example, this can occur via the T1ρ contrast or, respectively, via the contrast variation due to motion-sensitizing gradient fields 25 in the spin echo MR measurement sequence 62 (see FIGS. 3 and 4). The tissue elasticity determined with spatial resolution in Step S5 can be used for the elastography.

In Step S6 a check is made as to whether MR signals or, respectively, values for the tissue elasticity are required from an additional slice 30a. If this is the case, Steps S2-S5 are implemented again. Otherwise, the method ends in Step S7.

Figure 7:
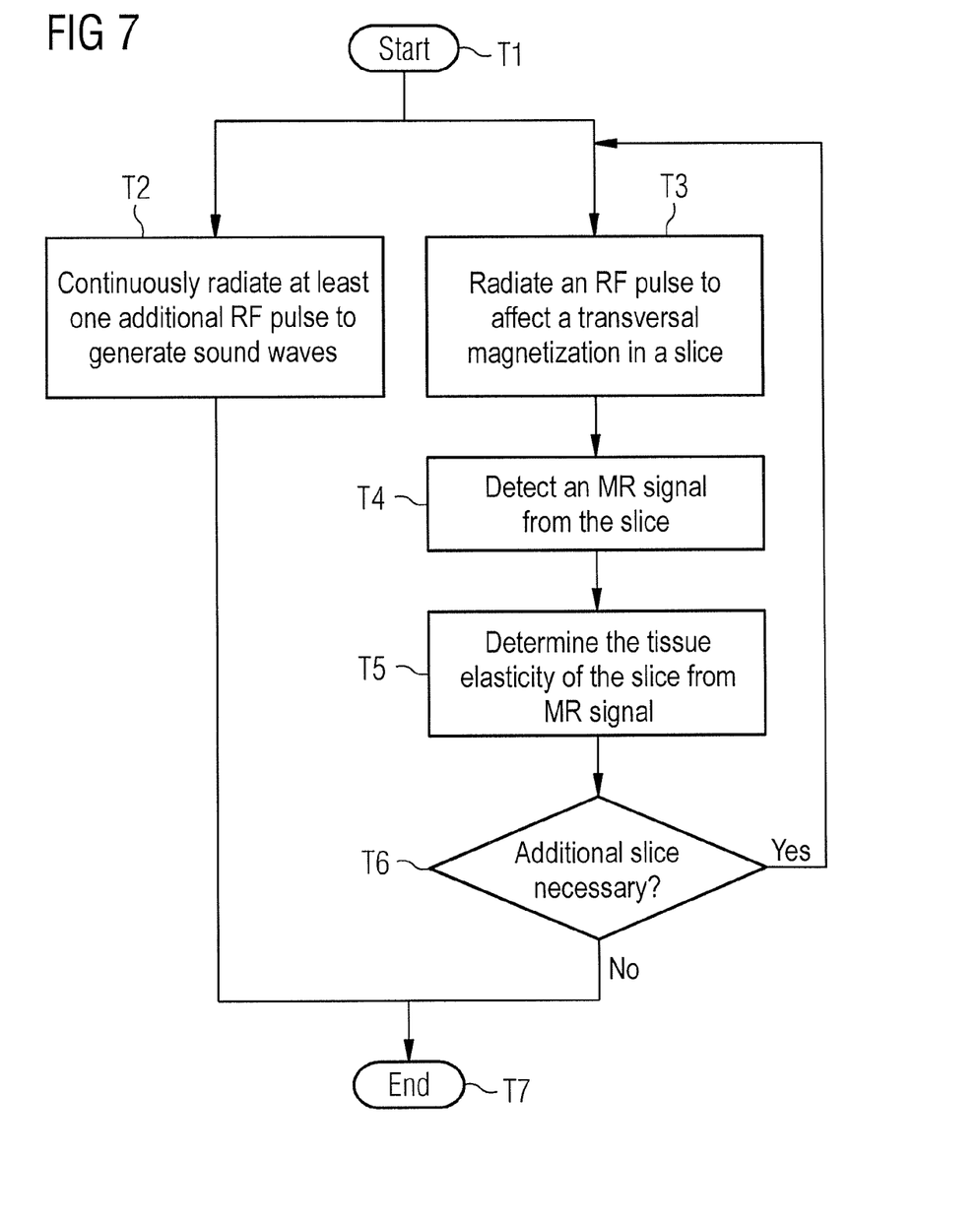
FIG. 7 is a flow chart of a further method according to the invention for elastography.

A flow chart of an additional method according to the invention is shown in FIG. 7. The radiation of the additional RF pulses 21 takes place continuously in FIG. 7 with the additional frequency 53 (Step T2). However, in the embodiment of FIG. 7 it is not necessary to trigger the generation of the shear waves 50 at the MR measurement sequence 61, 62. The MR measurement sequence 61, 62—i.e. the radiation of the RF pulses 20 and the detection phase 22 (Steps T3, T4)—takes place with whole-number multiples of the additional frequency 53. A defined phase relationship can therefore be achieved, for example between motion-sensitizing gradient fields 25 in the case of the spin echo MR measurement sequence 62 or the spin-lock preparation pulse 26 in the case of the spin-lock MR measurement sequence 61. In particular, in such an embodiment of FIG. 7 it can be advantageous to provide corresponding RF techniques which in particular enable a simultaneous radiation of the RF pulses 20, 21 to manipulate the transversal magnetization and the shear waves 50.

Naturally, the features of the previously described embodiments and aspects of the invention can be combined with one another. In particular, the features can be used not only in the described combinations but also in other combinations or independently without departing from the scope of the invention. While reference is made in the preceding predominantly to techniques in which the shear waves are generated by means of the at least one additional RF pulse 21, it should be understood that it is also possible to generate the shear waves by means of a non-ionizing laser pulse. In particular, features with regard to the time synchronization with the MR measurement sequences 61, 62 etc. can also be applied to this aspect of the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for elastography of a defined region of an examination subject using a magnetic resonance system that comprises a radio-frequency (RF) generator connected to an RF coil array and to an RF antenna, said method comprising:
   operating the RF generator to radiate an RF excitation pulse from the RF antenna into a defined region of an examination subject in the magnetic resonance system, configured to manipulate a transverse magnetization of nuclear spins in the defined region so as to cause said nuclear spins to emit magnetic resonance signals;
   operating the RF generator to radiate at least one additional RF pulse from the RF coil array into said defined region of said examination subject in said magnetic resonance system, with a spatial selectivity of an amplitude of said at least one additional RF pulse configured to generate shear waves that originate in said defined region;
   operating said coil array of said magnetic resonance system to detect said magnetic resonance signals from said defined region; and
   in a computerized processor supplied with said magnetic resonance signals, automatically reconstructing an image of said defined region from said magnetic resonance signals in which said shear waves are detectable, and detecting said shear waves in said magnetic resonance image and determining a value describing tissue elasticity in said defined region from said shear waves detected in magnetic resonance image, and making said value available at an output of said processor in electronic form.

2. A method as claimed in claim 1 comprising operating the RF generator to radiate said at least one additional RF pulse with a spatial selectivity of said amplitude to generate quasiplanar shear waves by sequential radiation of multiple additional RF pulses with a maximum of said amplitude at respective different locations, said different locations being spaced substantially parallel to a wave front of said quasiplanar shear wave.

3. A method as claimed in claim 2 comprising operating the RF generator to repeat the sequential radiation of said multiple additional radio-frequency pulses with an additional frequency.

4. A method as claimed in claim 3 comprising selecting said additional frequency dependent on at least one of a wavelength of said quasiplanar shear wave and a spatial resolution of the elastography, with said additional frequency being in a range between 20 and 400 Hz.

5. A method as claimed in claim 4 wherein said additional frequency is in a range between 50 and 150 Hz.

6. A method as claimed in claim 1 comprising operating the RF generator to radiate said RF pulse and to detect said magnetic resonance signals in an MR measurement sequence selected from the group consisting of spin echo sequences and spin-lock sequences.

7. A method as claimed in claim 6 comprising operating the RF generator to radiate said at least one additional RF pulse with a spatial selectivity of said amplitude to generate quasiplanar shear waves by sequential radiation of multiple additional radio-frequency pulses with a maximum of said amplitude at respective different locations, said different locations being spaced substantially parallel to a wave front of said quasiplanar shear wave, and to repeat the sequential radiation of the multiple additional RF pulses with an additional frequency, and selecting a repetition rate of said MR measurement sequence for different slices within said defined region, or for different defined regions, and said additional frequency, are matched to each other.

8. A method as claimed in claim 7 wherein said MR measurement sequence is a spin-lock sequence, with a spin-lock preparation pulse, and comprising radiating said at least one additional radio-frequency pulse during said spin-lock preparation pulse.

9. A method as claimed in claim 7 wherein said MR measurement sequence is a spin echo sequence, with motion-sensitizing gradient fields, and comprising radiating said at least one additional radio-frequency pulse during said motion-sensitizing gradient fields.

10. A method as claimed in claim 9 comprising operating the RF generator to radiate said at least one additional RF pulse with a spatial selectivity of said amplitude to generate quasiplanar shear waves by sequential radiation of multiple additional radio-frequency pulses with a maximum of said amplitude at respective different locations, said different locations being spaced substantially parallel to a wave front of said quasiplanar shear wave, and to repeat the sequential radiation of said multiple additional RF pulses with an additional frequency in a third quarter of a duration of said motion-sensitizing gradient fields.

11. A method as claimed in claim 1 comprising operating the RF generator to set at least one of a duration and an amplitude of said at least one additional RF pulse depending on an estimated amplitude of said shear wave.

12. A method as claimed in claim 1 comprising operating the RF generator to set at least one of a duration and an amplitude of said at least one additional RF pulse based on an estimated heating of tissue that is less than 1 K in said defined region.

13. A method as claimed in claim 1 comprising operating the RF generator to set at least one of a duration and an amplitude of said at least one additional RF pulse based on an estimated heating of tissue that is less than 10 mK in said defined region.

14. A method as claimed in claim 1 comprising operating the RF generator to set at least one of a duration and an amplitude of said at least one additional RF pulse based on an estimated heating of tissue that is approximately 1 mK in said defined region.

15. A method as claimed in claim 1 comprising operating the RF generator to set a carrier frequency of said at least one additional radio-frequency pulse to be different from a resonance frequency of said transverse magnetization.

16. A method as claimed in claim 1 comprising using a coil of said RF coil array as said RF antenna to radiate said RF excitation pulse.

17. A magnetic resonance (MR) system comprising:

an MR data acquisition scanner comprising a radio-frequency (RF) generator and an RF coil array and an RF antenna;

a computer configured to operate said RF generator and said RF coil of said MR data acquisition scanner to radiate an RF excitation pulse from said RF antenna into a defined region of an examination subject in a magnetic resonance system, configured to manipulate a transverse magnetization of nuclear spins in the defined region so as to cause said nuclear spins to emit magnetic resonance signals;

said computer being configured to operate said MR data acquisition scanner to radiate at least one additional RF pulse from said RF coil array into said defined region of said examination subject in said magnetic resonance system, with a spatial selectivity of an amplitude of said at least one additional RF pulse configured to generate shear waves that originate in said defined region;

said computer being configured to operate said RF coil array of MR data acquisition scanner to detect said magnetic resonance signals from said defined region; and said computer being configured to reconstruct an image of said defined region from said magnetic resonance signals in which said shear waves are detectable, and automatically detect said shear waves in said magnetic resonance image and determine a value describing tissue elasticity in said defined region based from said shear waves detected in said magnetic resonance image, and to make said value available in electronic form at an output of said computer.

18. An MR system as claimed in claim 17 wherein said RF antenna is a coil of said RF coil array.

* * * * *